(12) United States Patent
Mayr et al.

(10) Patent No.: US 12,259,065 B2
(45) Date of Patent: Mar. 25, 2025

(54) PINCH VALVE SYSTEM

(71) Applicant: Levitronix GmbH, Zurich (CH)

(72) Inventors: Peter Mayr, Baden (CH); Thomas Schneeberger, Bern (CH)

(73) Assignee: Levitronix GmbH, Zurich (CH)

( * ) Notice: Subject to any disclaimer, the term of this patent is extended or adjusted under 35 U.S.C. 154(b) by 0 days.

(21) Appl. No.: 17/885,331

(22) Filed: Aug. 10, 2022

(65) Prior Publication Data

US 2023/0077009 A1 Mar. 9, 2023

(30) Foreign Application Priority Data

Sep. 3, 2021 (EP) .................................... 21194899

(51) Int. Cl.
*F16K 7/04* (2006.01)
*F16K 31/08* (2006.01)

(52) U.S. Cl.
CPC ............ *F16K 7/045* (2013.01); *F16K 31/082* (2013.01)

(58) Field of Classification Search
CPC .... F16K 7/045; F16K 31/082; F16K 37/0041; A61M 39/28
See application file for complete search history.

(56) References Cited

U.S. PATENT DOCUMENTS

| | | | | |
|---|---|---|---|---|
| 3,511,469 | A * | 5/1970 | Bell | F16K 7/045 251/285 |
| 4,191,359 | A * | 3/1980 | Andersson | A61M 39/284 251/9 |
| 6,386,505 | B2 * | 5/2002 | Schob | F16K 31/082 251/7 |
| 9,803,754 | B2 * | 10/2017 | Thompson | F16K 31/0655 |
| 10,183,107 | B2 * | 1/2019 | Utsugida | A61M 1/3626 |
| 10,234,058 | B2 * | 3/2019 | Junk | F16K 31/0627 |
| 11,131,398 | B2 * | 9/2021 | Srikanth | F16K 31/1221 |
| 11,215,288 | B2 * | 1/2022 | Bargh | F16K 7/045 |

(Continued)

FOREIGN PATENT DOCUMENTS

EP 1132108 A1 9/2001

OTHER PUBLICATIONS

European Search Report of corresponding European Application No. EP 21 19 4899 dated Mar. 3, 2022 with an English translation of Categories Section.

*Primary Examiner* — Umashankar Venkatesan
(74) *Attorney, Agent, or Firm* — Global IP Counselors, LLP (57) ABSTRACT

A pinch valve system includes a closing element arranged in an axial direction and includes a closing piece, a permanent magnetic holding device to hold the closing element by a permanent magnetic force in an open or closed position, without energy being supplied to the permanent magnetic holding device, an electromagnetic actuating device to carrying out a switching process, with which the closing element is configured to be moved from the open position to the closed position or from the closed position to the open position, an energy storage device to store an electrical energy which is sufficient to carry out the switching process, and a controller programmed with a predetermined rest position, which is the open or closed position, and the controller configured to trigger the switching process with which the closing element is brought to the rest position by the energy stored in the energy storage device.

16 Claims, 7 Drawing Sheets

(56) References Cited

U.S. PATENT DOCUMENTS

| | | | |
|---|---|---|---|
| 11,458,239 B2* | 10/2022 | Grober | A61M 1/367 |
| 2012/0018654 A1* | 1/2012 | Wennberg | F16K 7/06 |
| | | | 251/9 |
| 2017/0304605 A1* | 10/2017 | Newell | A61M 39/28 |
| 2020/0370670 A1 | 11/2020 | Kraus et al. | |
| 2022/0213978 A1* | 7/2022 | Choi | F16K 37/0025 |

* cited by examiner

PINCH VALVE SYSTEM

CROSS-REFERENCE TO RELATED APPLICATION

This application claims priority to European Application No. 21194899.7 filed Sep. 3, 2021, the contents of which are hereby incorporated by reference in their entirety.

BACKGROUND

Field of the Invention

The present disclosure relates to a pinch valve system for clamping off a tube in a fluid system.

Background Information

Conventional fluid systems, for example for biological liquids, typically comprise a pumping device for the fluid to be conveyed, which is connected via tubes to a circuit or to other components of the fluid system, such as storage tanks or filter devices. Examples of such fluid systems are plants in biotechnology or in the pharmaceutical industry, which comprise a bioreactor in which proteins or other biological substances are produced in a cell broth and are removed from the process. Another example is heart-lung machines, which are connected to the patient's blood circulation during heart surgery, for example, to take over the function of the heart and maintain the blood circulation. It is very important that there are, if possible, no air bubbles in the blood that is pumped into the patient's circulation, because these represent serious hazards to the patient. Therefore, a bubble detector and a pinch valve system are usually provided downstream of the pump in heart-lung machines. As soon as the bubble detector detects an air bubble, the pinch valve system must clamp off the tube through which the conveyed blood flows into the patient's body as quickly as possible, and thus interrupting the blood supply to the patient so that the air bubble cannot enter the body's circulation system.

But also, in other fluid systems it is often a necessity that a tube can be clamped off as quickly and reliably as possible to prevent further flow through the tube. Thus, the pinch valve systems used for this purpose serve as on/off switches for the flow connection between components of the fluid system.

There are numerous designs of conventional pinch valve systems for clamping off a tube. A particularly efficient and reliable pinch valve system is disclosed in EP-A-1 132 108. This pinch valve system comprises a movably arranged closing element with a closing piece for clamping off the tube, a permanent magnetic holding device which is arranged and designed in such a way that it can hold the closing element in two different stable equilibrium positions, namely an open position and a closed position, without energy having to be supplied to the permanent magnetic holding device for holding in the respective equilibrium position, and actuating means for moving the closing element from the open position to the closed position.

The permanent magnetic holding device is designed in such a way that two stable equilibrium positions exist for the closing element, namely on the one hand the open position, in which a tube inserted into the pinch valve system is not clamped or only slightly clamped so that the liquid can flow through the tube, and on the other hand a closed position, in which the tube is clamped off by the closing piece of the closing element so that no more liquid can flow through the tube. No electrical energy is required to hold the closing element in the two equilibrium positions. The closing element is held in the two equilibrium positions purely passively, i. e., permanently magnetically, which is a very considerable advantage in terms of energy consumption. This means that it is a bistable device which requires energy only for switching from one of the equilibrium positions to the other equilibrium position, but not for holding in the respective stable equilibrium position.

In addition, no spindle drives or other self-locking drives are necessary to actuate the pinch valve system, which is why the pinch valve system is structurally simple and very compact.

The actuating means comprise a coil which is arranged such that it can exert on the closing element an electromagnetic force acting in the direction of the closed position or in the direction of the open position. By activating the coil, an electromagnetic force is generated in addition to the permanent magnetic holding force, which deflects the closing element so far from its one stable equilibrium position that it takes up its other stable equilibrium position. Therefore, the coil only needs to be activated if the closing element is to be brought from the open position to the closed position or vice versa from the closed position to the open position.

SUMMARY

It has been determined that even though the pinch valve system disclosed in EP-A-1 132 108 has proved very well in practice, there is potential for improvement.

Starting from this state of the art, it is therefore an object of the disclosure to further improve a pinch valve system of the type described above. In particular, a higher operational safety and a high flexibility can be realizable.

The subject matter of the disclosure meeting this object is characterized by the features of the embodiments described herein.

According to an embodiment of the invention, a pinch valve system for clamping off a tube in a fluid system is therefore proposed, having a closing element arranged movably in an axial direction and comprising a closing piece for clamping off the tube, having a permanent magnetic holding device which is designed in such a way that it can hold the closing element by a permanent magnetic force in two different stable equilibrium positions, namely in an open position and in a closed position, without energy having to be supplied to the permanent magnetic holding device for holding in the respective equilibrium position, and having an electromagnetic actuating device for carrying out a switching process, with which the closing element is moved from the open position to the closed position or from the closed position to the open position. An energy storage device and a control unit are provided, wherein an electrical energy can be stored in the energy storage device which is at least sufficient to carry out one switching process, wherein a rest position, which is the open position or the closed position, can be predetermined for the control unit, and wherein the control unit can trigger a switching process with which the closing element can be brought into the rest position by the energy stored in the energy storage device.

In the case of the pinch valve system according to an embodiment of the invention, it is thus possible to bring the closing element of the pinch valve system into the predeterminable rest position even in the event of a complete failure of the external energy supply, for example in the event of a mains interruption. In any case, the energy storage device of the pinch valve system has stored so much energy that at least one switching process is still possible even in the event of a failure of the external energy supply. Thus, it is possible in any case to bring the closing element into the desired rest position even without an external energy supply. This means an enormous increase in operational reliability.

In addition, the pinch valve system according to an embodiment of the invention is characterized by a high degree of flexibility, because the predeterminable rest position can be the open position or the closed position. In dependence on the specific application, it can be desirable or even necessary that the closing element is brought into the open position in the event of a failure of the external energy supply so that the fluid can flow through the tube. In other applications, it can be desirable or even necessary that the closing element is brought into the closed position in the event of a failure of the external energy supply so that the tube is clamped off and a further flow of the fluid through the tube is reliably prevented. The selection of whether the rest position is the open position or the closed position can, for example, be made electronically, electromechanically or by software.

According to a particularly preferred embodiment, the closing element, the holding device, the actuating device, the energy storage device, and the control unit (8) are arranged in a common housing, the housing having a connection for connecting to an external energy source. This embodiment is extremely compact and particularly easy to handle. The connection for connecting to an external energy source can additionally be used for control lines or signal lines with which the pinch valve system can be controlled or programmed.

Preferably, a monitoring sensor is provided in the common housing, with which an interruption of the energy supply by the external energy source can be detected. The monitoring sensor integrated in the housing can therefore detect when the energy supply by the external energy source fails completely or is no longer sufficient. For example, the monitoring sensor can detect an interruption in the supply voltage or mains current which is provided by the external energy source. As soon as an interruption in the supply voltage or current is detected, this information is passed on to the control unit. The control unit checks whether the closing element is in the open position or in the closed position, and which is the predetermined rest position for the closing element. If the closing element is not in the desired rest position, the control unit triggers a switching process which brings the closing element into the rest position. In any case, sufficient energy is stored in the energy storage device to carry out at least one switching process, even if the external energy source can no longer provide any energy.

In a preferred embodiment, the permanent magnetic holding device comprises a permanent magnetic ring which surrounds the closing element. With this permanent magnetic ring, the closing element can be held in either of the two stable equilibrium positions by permanent magnetic forces without energy having to be supplied to the pinch valve system, e.g., in the form of electric current. Preferably, the holding device is also designed without springs for holding the closing element in the stable equilibrium positions.

According to a preferred embodiment, the energy storage device is designed as an intermediate circuit for the energy supply of the actuating device. The energy storage device can comprise at least one capacitor, the capacity of which is sufficiently large to supply the actuating device with electrical energy for at least one switching process if the external energy supply fails. Due to this large energy storage device, the energy source which supplies the intermediate circuit with electrical energy can also be advantageously dimensioned smaller.

Furthermore, it is preferred that a position sensor is provided for determining the position of the closing element.

It is a further advantageous measure that a measuring sensor is provided for determining the electrical energy stored in the energy storage device.

It is also preferred that a current sensor is provided for determining a switching current, the switching current being the current required for the switching process.

For example, the switching current can be a closing current, the closing current being the current which is required for the switching process from the open position to the closed position. For example, the switching current can be an opening current, the opening current being the current which is required for the switching process from the closed position to the open position.

The current fed into the actuating device can be determined by the current sensor over the complete switching process, i.e., over the entire stroke movement of the closing element from the open position to the closed position—or vice versa. This information can be used, for example, to determine whether a tube is inserted in the pinch valve system or not.

In the case of this embodiment, it is particularly possible that a tube detection can be carried out on the basis of the switching current. For this purpose, for example, correlations can be stored in the control unit in an assignment table (lookup table) as to which current is required for which tube type in order to carry out a switching process from the open position to the closed position and/or from the closed position to the open position. For example, the tube type can contain information about the respective material of the tube, its diameter, its wall thickness and, if necessary, other parameters. On the basis of the switching current determined by measurement and, if desired, the signal from the position sensor, it is then possible to identify the tube inserted in the pinch valve system.

According to a preferred embodiment, two lateral openings are disposed in the housing for receiving a tube, wherein a closing cover is provided which is connected to the housing by an articulated joint, and can be moved back and forth between a first position and a second position, wherein in the first position the tube can be inserted into the lateral openings, and wherein in the second position the tube is fixed relative to the housing of the pinch valve system.

Preferably, a tube pinch element is arranged in the closing cover for cooperation with the closing piece of the closing element, in such a way that the tube can be clamped between the closing piece and the tube pinch element when the closing cover is in the second position.

Furthermore, it is a preferred measure that the tube pinch element is designed and arranged to be replaceable, so that the pinch valve system can be easily adapted to different types of tubes and, in particular, to different outer diameters and/or inner diameters of the tube.

It is a preferred embodiment that a recess is disposed in the closing cover into which the tube pinch element can be inserted. As a result, the tube pinch element can be replaced in a particularly simple and quick manner and, in particular, without the use of a tool.

Furthermore, it is preferred that a protective element movable in the axial direction is provided, which is loaded by a spring in such a way that the protective element covers the two lateral openings when the closing cover is in the first position or in the second position and no tube is inserted into the pinch valve system. This protective element serves in particular as finger protection for the operating personnel, so that there is no unintentional reaching into the lateral openings, for example, if no tube is inserted into the pinch valve system, or when inserting a tube. When inserting a tube, the protective element is moved in the axial direction by the tube against the force of the spring until the tube lies in the two lateral openings. Subsequently, the closing cover is brought in the second position so that the tube is fixed between the tube pinch element and the closing piece.

As a further advantageous measure, a securing element can be provided on the housing with which the closing cover can be fixed in the second position. In this way, an unintentional removal of the tube from the pinch valve system can be prevented.

Further advantageous measures and embodiments of the invention are described herein.

BRIEF DESCRIPTION OF THE DRAWINGS

Embodiments of the invention will be explained in more detail with reference to the drawings.

DETAILED DESCRIPTION

Figure 1:
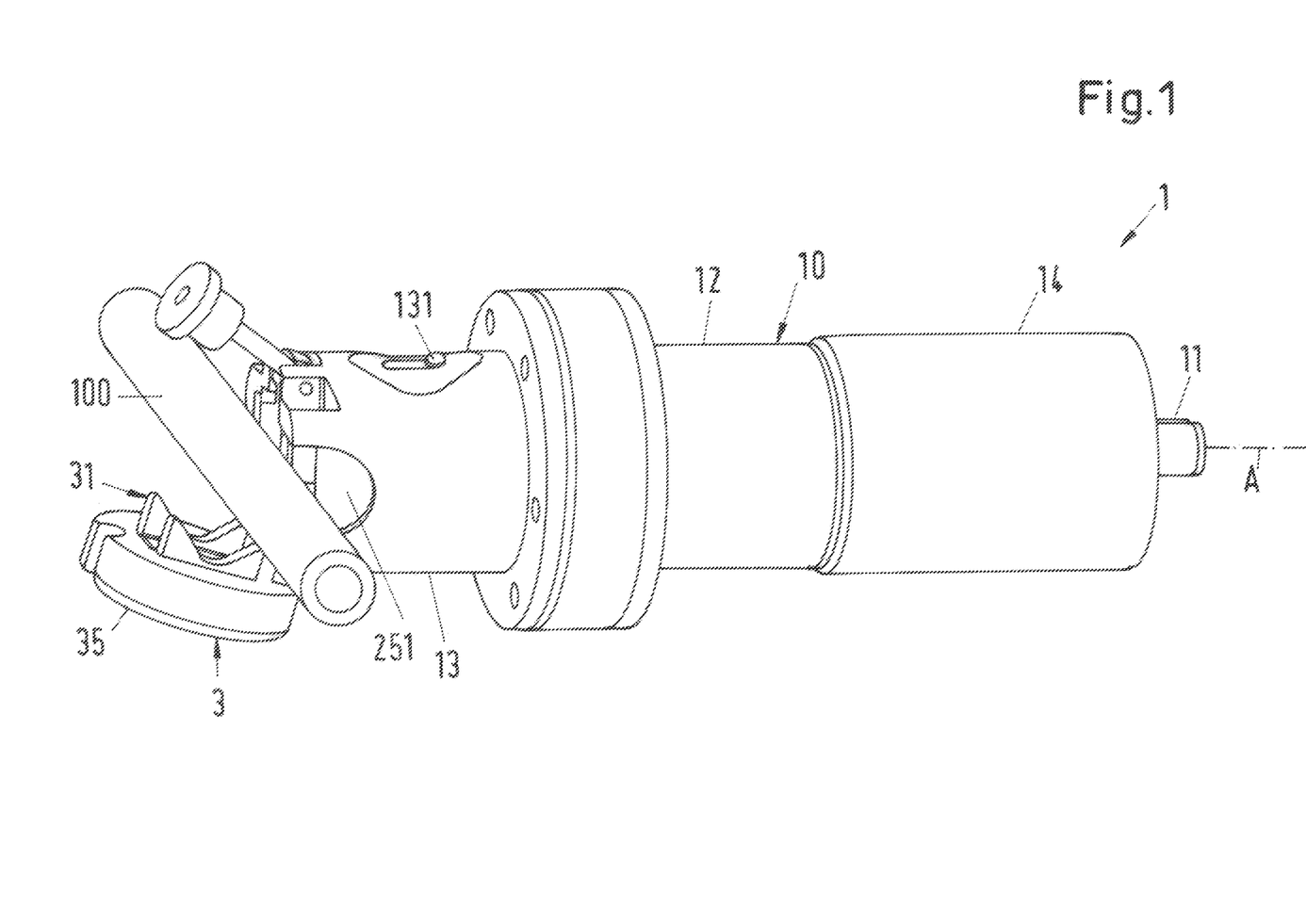
FIG. 1 illustrates an embodiment of a pinch valve system according to the invention in a perspective view.
Figure 2:
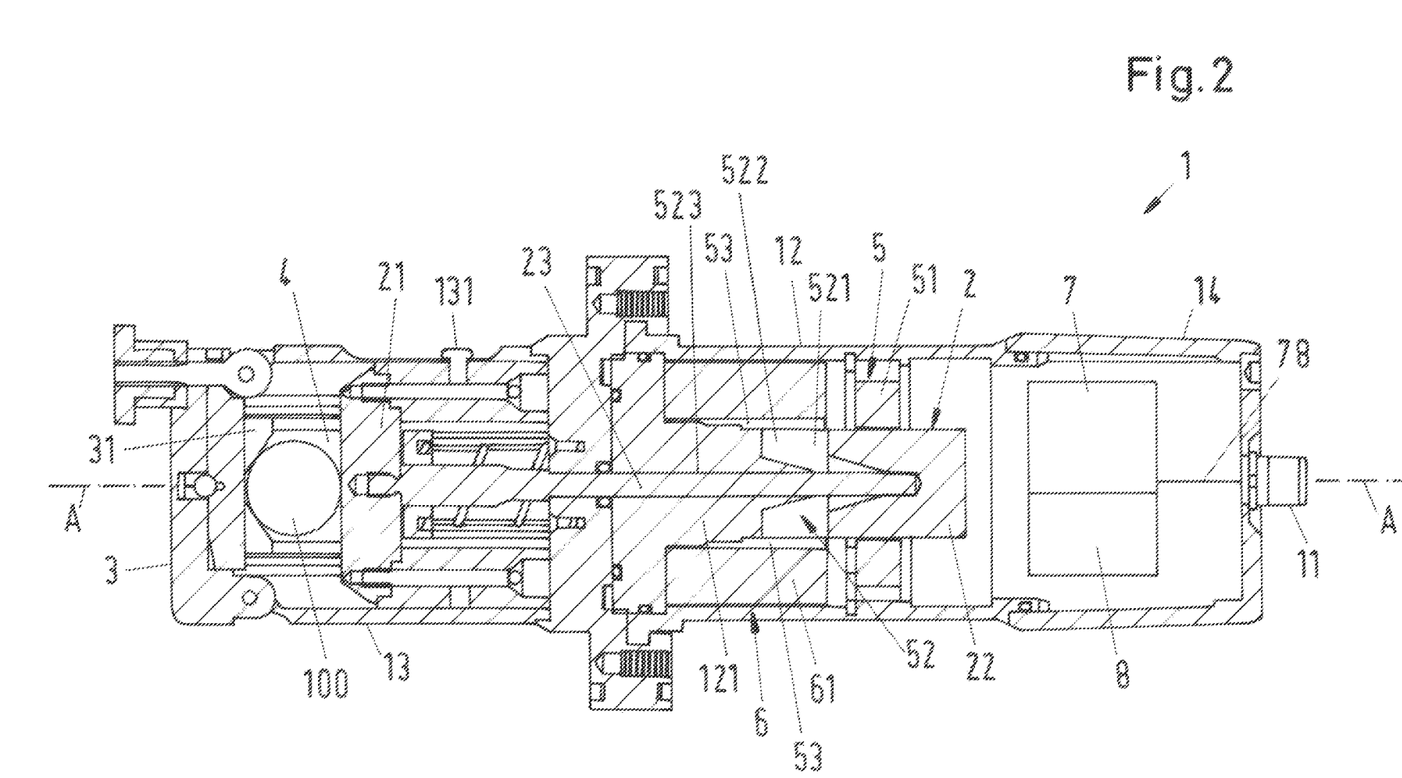
FIG. 2 illustrates a sectional representation of the embodiment in a section in the axial direction.
Figure 5:
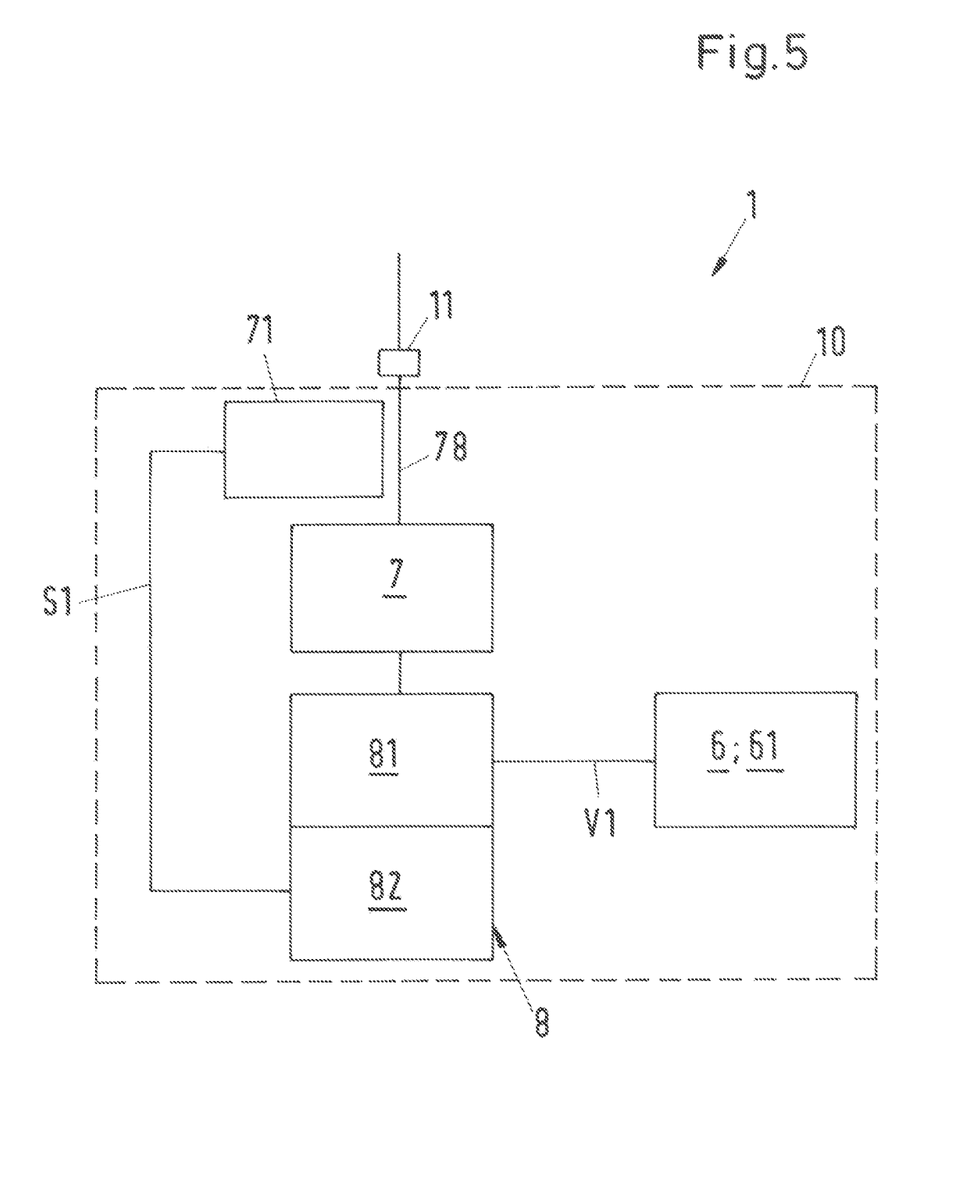
FIG. 5: illustrates a schematic representation of the embodiment.

FIG. 1 shows a perspective representation of an embodiment of a pinch valve system according to the invention which is designated as a whole with the reference sign 1. For a better understanding, FIG. 2 shows a sectional representation of the embodiment in a section in the axial direction A and FIG. 5 shows a schematic representation of the embodiment.

The pinch valve system 1 serves to clamp off a tube 100 in a fluid system, wherein the tube 100 can be inserted into the pinch valve system 1 and fixed therein.

The pinch valve system 1 comprises a closing element 2, which is arranged to be movable in an axial direction A. The closing element 2 comprises a closing piece 21 for clamping off the tube 100, which can cooperate with a tube pinch element 31 arranged in a closing cover 3 of the pinching valve system 1. The closing piece 21 and the tube pinch element 31 limit, with respect to the axial direction, a receptacle 4 for the tube 100, which is arranged between the closing piece 21 and the tube pinch element 31, and into which the tube 100 can be inserted.

The pinch valve system 1 further comprises a permanent magnetic holding device (permanent magnetic holder) 5, an electromagnetic actuating device (electromagnetic actuator) 6, an energy storage device (energy storage) 7 and a control unit (electronic controller) 8.

The closing element 2, the holding device 5, the actuating device 6, the energy storage device 7 and the control unit 8 are arranged in a common housing 10 of the pinch valve system 1, wherein a connection 11 is provided on the housing, with which the pinch valve system 1 can be connected to an external energy source. The connection 1 can additionally be used for control lines or signal lines with which the pinch valve system 1 can be actuated or programmed, or data and other information can be exported from the pinch valve system 1.

The permanent magnetic holding device 5 is designed in such a way that it can hold the closing element 2 by a permanent magnetic force in two different stable equilibrium positions, namely in an open position and in a closed position, without energy having to be supplied to the permanent magnetic holding device 5 for holding in the respective equilibrium position. In the case of this embodiment, the holding device 5 comprises a permanent magnetic ring 51 for this purpose, which is arranged around the closing element 2.

In the open position shown in FIG. 2, the tube 100 inserted in the receptacle 4 is not clamped or is clamped only very slightly, so that the liquid or the fluid can flow through the tube 100, but the tube 100 is fixed. In the closed position, the tube 100 is clamped between the closing piece 21 and the tube pinch element 31 in such a way that no more liquid can flow through the tube 100. In the open position (FIG. 2), the flow cross-section for the liquid in the tube 100 is at a maximum. For closing, the closing element 2 and thus also the closing piece 21 are moved to the left according to the representation (FIG. 2), and thereby compressing the tube 100 in such a way that the flow cross-section becomes zero. In this closed position of the closing element 2, the tube 100 is then clamped off.

The electromagnetic actuating device 6 is designed to carry out a switching process with which the closing element 2 can be moved from the open position to the closed position or from the closed position to the open position. For this purpose, the electromagnetic actuating device 6 comprises at least one coil 61, which can be actuated by the control unit 8 to carry out a switching process. An additional electromagnetic force is exerted on the closing element 2 by the coil 61 for a switching process, which force is strong enough to deflect the closing element from its one stable equilibrium position (e.g., the open position) to such an extent that the closing element 2 takes up the other of its two stable equilibrium positions (e.g., the closed position).

It is a substantial aspect that the permanent magnetic holding device 5 can hold the closing element 2 in both equilibrium positions (open position and closed position) without energy, e.g., electric current having to be supplied for this purpose. During holding, the pinch valve system 1 does not need any electrical energy, which is why it is enormously economical in terms of energy consumption in the two equilibrium positions.

The permanent magnetic holding device 5 (see FIG. 2) is arranged in an actuator housing 12, which forms a part of the common housing 10. The actuator housing 12 is made of a ferromagnetic material. The holding device 5 has a central passage 52 for receiving the closing element 2. The passage 52 extends in the axial direction A and has a first cylindrical region 521, to which a conical region 522 is connected, which then merges into a second cylindrical region 523, the diameter of which is smaller than the diameter of the first cylindrical region 521. The conical region 522 and the second cylindrical region 523 are limited by an extension 121 of the actuator housing 12, which serves as a magnetic reflux for guiding the magnetic flux and is designed in a ferromagnetic manner. The extension 121 has a conical boundary surface which extends obliquely to the axial direction A and can cooperate with a surface of the closing element 2 which is also conical in shape. A sleeve 53, which is made of a non-ferromagnetic material, for example plastic, is inserted into the first cylindrical region 521.

The closing element 2 comprises a cylindrically designed head 22, the outer diameter of which is adapted to the inner diameter of the sleeve 53 in the first cylindrical region 521 of the passage 52, so that the head 22 can enter the sleeve 53 and is guided through the latter. The head 22 is made of a ferromagnetic material and has the conically designed surface at its left end according to the representation (FIG. 2), which cooperates with the conical boundary surface of the extension 121. Furthermore, a rod 23 is attached to this end of the head 22, which extends in the axial direction A through the second cylindrical region 523 of the passage 52 and to whose left end, according to the representation (FIG. 2), the closing piece 21 is fixed.

Furthermore, the permanent magnetic ring 51 is provided in the actuator housing 12 which is arranged to surround the head 22 of the closing element 2.

The coil 61 is provided in the actuator housing 12 in the axial direction A adjacent to the permanent magnetic ring 51, which coil serves as an actuating means or device (actuator) to move the closing element 2 from its open position to its closed position or vice versa. The coil 61 encloses the passage 52, so that the coil axis extends in the axial direction A. Therefore, when supplied with current, the coil 61 can exert an electromagnetic force directed in the axial direction A on the closing element 2, wherein this electromagnetic force can be directed to the right or to the left depending on the direction of the current according to the representation (FIG. 2).

The coil 61 adjoins the extension 121 of the actuator housing 12 with its axial end facing away from the permanent magnetic ring 51. The coil 61 is further signal-connected to the control unit 8 so that the control unit 8 can supply the coil 61 with electrical energy and can trigger a switching process.

With regard to the existence of the two stable equilibrium positions in which the closing element 2 can be held by permanent magnetic forces without further energy supply, as well as the switching processes in which the closing element 2 can be moved from the closed position to the open position or from the open position to the closed position by electromagnetic forces generated by the coil 61, reference is made to the EP-A-1 132 108 already mentioned and the detailed explanations to be found there.

According to an embodiment of the invention, the energy storage device 7 is designed in such a way that an electrical energy can be stored in the energy storage device which is at least sufficient to carry out one switching process. Furthermore, a rest position, which is the open position or the closed position, can be predetermined for the control unit 8, wherein the control unit 8 can trigger a switching process with which the closing element 2 can be brought into the rest position by the energy stored in the energy storage device 7.

In the following, this is explained in more detail on the basis of the embodiment and with reference to FIG. 1, FIG. 2, and FIG. 5.

In the embodiment described here, the pinch valve system 1 is designed as a fully integrated bistable system in which no return springs are provided for the switching processes or for the holding in each of the two stable equilibrium positions. The common housing 10 comprises the actuator housing 12, a closure housing 13 and a protective housing 14, wherein the actuator housing 12 is arranged between the closure housing 13 and the protective housing 14 with respect to the axial direction A. The actuator housing 12, the closure housing 13 and the protective housing 14 are firmly connected to each other, for example by screws or other fastening means or device, so that they form the common housing 10.

The closure housing 13 has the closing cover 3 at the axial end of the closure housing 13, which faces away from the actuator housing 12. The closing cover 3 is connected to the closure housing 13 by an articulated joint and can be moved back and forth between a first position and a second position. In the first position (see also FIG. 3), the tube 100 can be inserted into the receptacle 4. In the second position (see also FIG. 4), the tube 100 is fixed relative to the common housing 10, namely between the tube pinch element 31 and the closing piece 21. Preferably, an indicator 131 is disposed on the closure housing 13, which indicates, recognizable from the outside, whether the closing element 2 is in its open position or in its closed position.

The energy storage device 7 and the control unit 8 are arranged in the protective housing 14. Furthermore, the connection 11 is provided on the protective housing 14, via which the pinch valve system 1 can be connected to an external energy source (not represented). Furthermore, the actuation and/or the programming of the control unit 8 can be carried out via the connection 11. The connection 11 is connected to the energy storage device 7 and/or the control unit 8 via an electrical connection 78.

As represented in FIG. 5, the control unit 8 comprises a power unit 81 and an open loop control unit 82. The power unit 81 comprises in particular the power electronics, which supply the coil 61 of the actuating device 6 with energy, in particular with current, if a switching process is to be carried out. For this purpose, the power unit 81 is connected to the coil 61 via a connection V1. The open loop control unit 82 comprises the controls or the regulators for the operation of the pinch valve system 1 and optionally memory modules, processing modules or evaluation modules for the operation of the pinch valve system 1.

Particularly preferably, the energy storage device 7 is designed as an intermediate circuit for the energy supply of the actuating device 6. On the one hand, the energy storage device 7 can be connected to the external energy source via the electrical connection 78 and the connection 11, and on the other hand, it is connected to the coil 61 of the actuating device 6 via the connection V1. For example, the external energy source is a supply voltage, for example the mains voltage, or another voltage source or a current source.

Particularly preferably, the energy storage device 7 comprises at least one capacitor for storing electrical energy, wherein the capacitor or—in the case of several capacitors—the entirety of the capacitors—has/have a capacity which is large enough that even in the event of a failure of the energy supply by the external energy source, sufficient electrical energy is stored in the energy storage device 7 to carry out at least one switching process. The energy stored in the energy storage device 7 is preferably greater than the path integral over the force along the stroke movement of the closing element 2 from the open position to the closed position.

The power electronics in the power unit 81 can be designed in any manner known per se that is suitable for actuating the coil 61. For example, the power electronics can be designed as an H-bridge with overvoltage protection, wherein the H-bridge is supplied with the intermediate circuit voltage provided by the energy storage device 7.

Preferably, a monitoring sensor 71 is disposed in the common housing 10, with which an interruption of the energy supply can be detected, i.e., a failure of the energy supplied by the external energy source. Generally, an external sensor could also be provided which transmits a signal to the control unit 8, if there is a failure with the external energy source, but the monitoring sensor 71 disposed internally in the common housing 10 is preferred. The monitoring sensor 71 is preferably arranged in the protective housing 14 and is signal-connected to the control unit 8, more precisely to the open loop control unit 82 of the control unit 8, via a signal line S1. The monitoring sensor 71 is preferably designed as a current sensor or a voltage sensor and arranged such that it can detect a fault in the supply from the external power source. For example, a fault in the supply can be a mains interruption or a collapse of the supply voltage, e.g., the mains voltage or a lack of current flow.

For the operation of the pinch valve system 1, the tube 100 is inserted into the receptacle 4, and the closing cover 3 is brought into the second position, in which the tube is fixed between the closing piece 21 and the tube pinch element 31. The desired rest position is predetermined to the open loop control unit 82 of the control unit 8, which is the open position or the closed position. Thus, it is predetermined for the control unit 8 whether the closing element 2 is to be brought to the open position or to the closed position when the external power supply fails.

If now a failure of the external energy supply, for example a lack of the supply voltage, is detected by the monitoring sensor 71, this information is transmitted to the open loop control unit 82 of the control unit 8. The control unit 8 checks whether the closing element 2 is in the predetermined rest position. If so, it is not necessary to take any further steps because no energy supply is required to keep the closing element 2 in the rest position. If the closing element 2 is not in the predetermined rest position, the open loop control unit 82 sends a command to the power unit 81 that a switching process must be carried out. The electrical energy required for this switching process is available in the energy storage device 7 so that the actuating device 6 can move the closing element 2 into the rest position. As soon as the closing element 2 is in the rest position, no further energy supply is required to keep the closing element 2 in the rest position.

Figure 6:
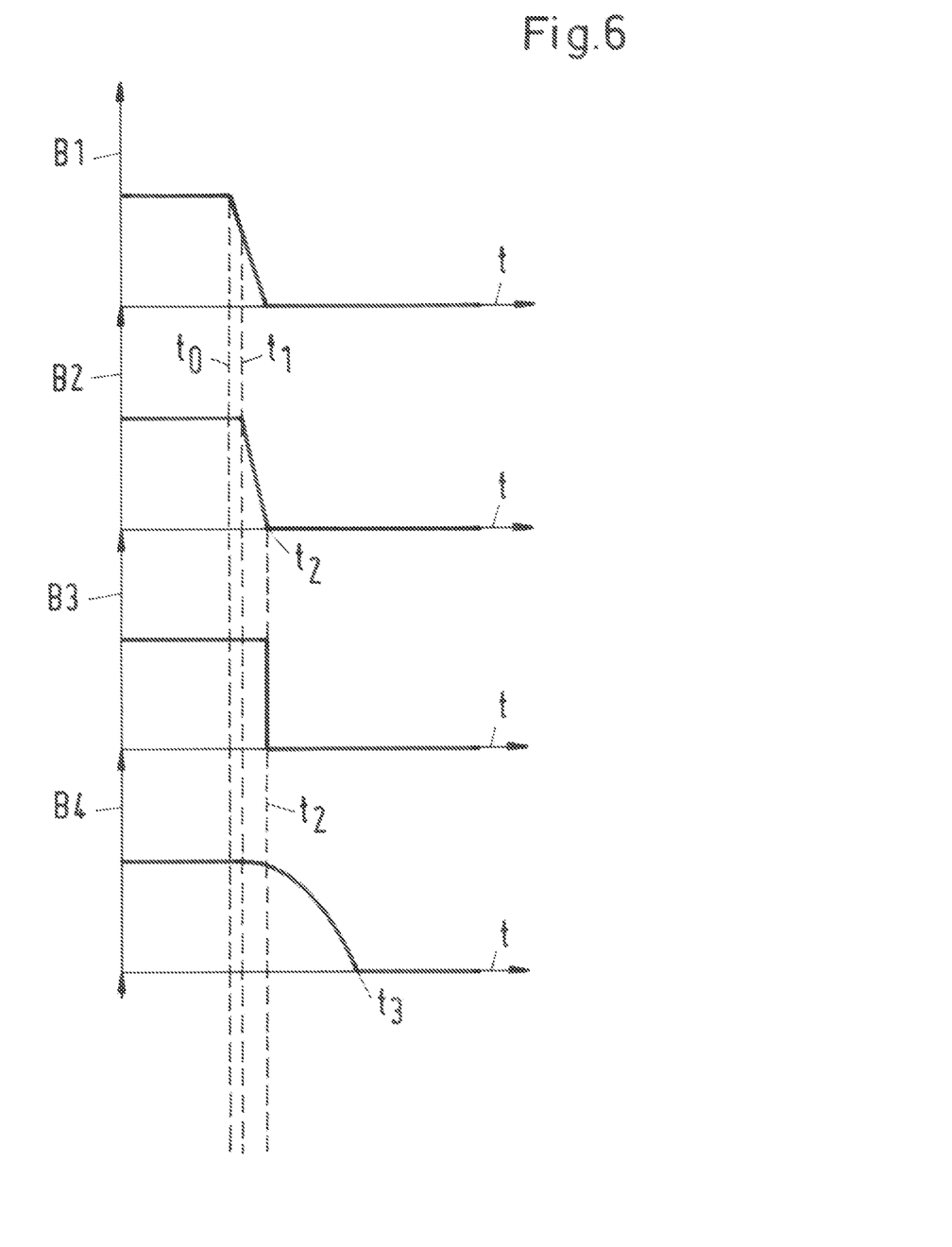
FIG. 6: illustrates several diagrams for explaining the operation of the embodiment.

This operation is exemplarily illustrated in FIG. 6 by several schematic diagrams in which the time t is plotted on the horizontal axis in each case. The following values are plotted on the vertical axis, viewed from top to bottom: the supply voltage B1 provided by the external energy source, the detection of the mains interruption B2 (loss of the external energy supply or the supply voltage), the action of the open loop control unit B3, the energy B4 in the energy storage device 7.

The embodiment illustrated in FIG. 6 refers to the case that the closing element 2 is not in the rest position but in the other of the two stable equilibrium positions when the external energy supply is lost—here, for example, a mains interruption in which the supply voltage is lost.

At time $t_0$, there is an interruption or a loss of the supply voltage B1. At time $t_1$, the monitoring sensor 71 detects the failure of the external energy supply B2 and transmits this information to the open loop control unit B3. The action of the open loop control unit B3 takes place at time $t_2$, namely initiating a switching process by the electrical energy stored in the capacitor of the energy storage device 7.

The energy B4 stored in the energy storage device 7 decreases due to the switching process. The switching process is completed at time $t_3$ and the closing element 2 has reached the predetermined rest position.

It is understood that the energy B4 which is stored in the energy storage device 7 represented as an example in the bottom diagram of FIG. 6 does not have to reach the value zero at time $t_3$ but can also have a value other than zero. This means that it is entirely possible that the energy storage device 7 is not completely discharged at time $t_3$, but that energy can still be stored in the energy storage device 7.

Figure 3:
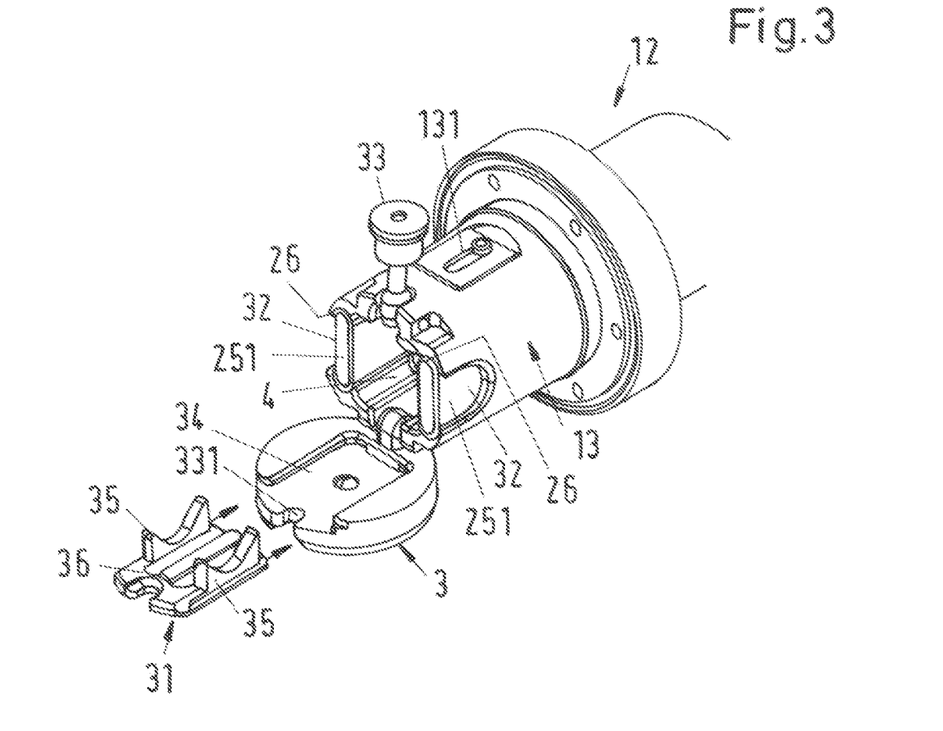
FIG. 3: illustrates a perspective representation of the closing cover of the embodiment and the lateral openings for receiving a tube.
Figure 4:
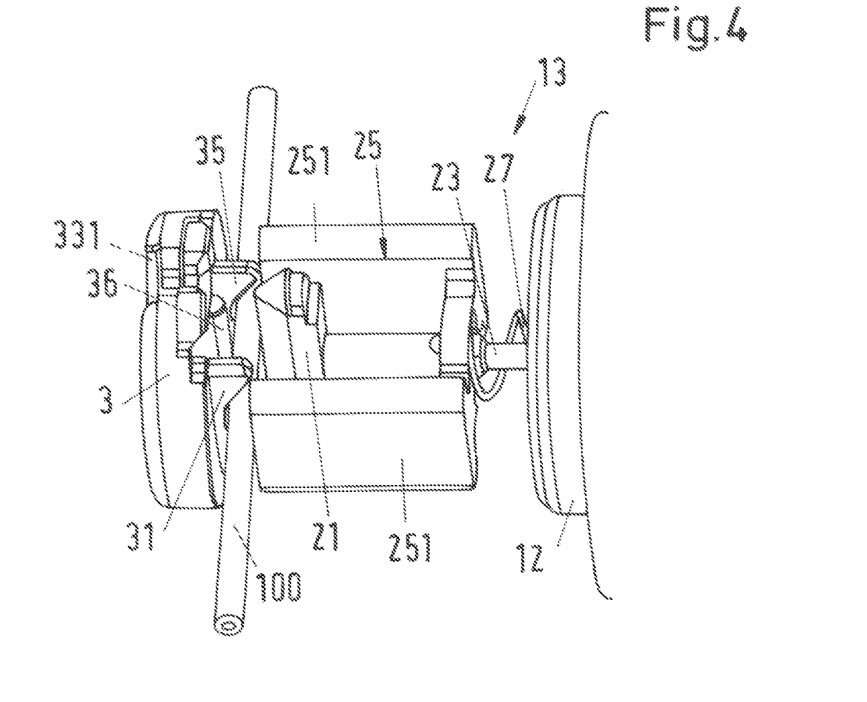
FIG. 4: illustrates a perspective representation of the protective element of the embodiment.

In the following, a preferred embodiment of the closure housing 13 with the closing cover 3 is explained on the basis of FIG. 3 and FIG. 4. FIG. 3 shows a perspective representation of the closure housing 13 with the closing cover 3 in the first position, in which the tube 100 can be inserted into or removed from the receptacle 4 of the pinch valve system 1 (the tube is not represented in FIG. 3). FIG. 4 shows the closing cover 3 in the second position, in which the tube 100 is fixed in the receptacle 4. Here, the tube 100 is clamped between the tube pinch element 31 and the closing piece 21. For a better understanding, only the closing cover 3 of the closure housing 13 is represented in FIG. 4; the rest is removed to allow a view of the interior.

In the closure housing 13, two lateral openings 32 are provided at the side of the receptacle 4, through which the tube 100 can leave the closure housing 13 when the closing cover 3 is in the second position. In this second position of the closing cover 3, the lateral openings 32 thus form the two passages at which the tube 100 penetrates the common housing 10, more precisely the closure housing 13 of the common housing 10.

The closing cover 3 is arranged at the axial end of the closure housing 13 and is connected to the closure housing 13 by an articulated joint, so that the closing cover 3 can be swiveled or tilted by approximately 90° from the first position (FIG. 3) to the second position (FIG. 4). Furthermore, a securing element 33 (FIG. 3) is provided on the closure housing 13, with which the closing cover 3 can be fixed in the second position, so that an unintentional opening of the closing cover 3—i.e., an unintentional leaving of the second position—can be safely avoided. For example, the securing element 33 is designed as a knurled screw which can cooperate with a groove 331 in the closing cover 3 if the closing cover 3 is in the second position. The knurled screw is received by the groove 331 in the second position of the closing cover. By tightening the knurled screw, the closing cover 3 can be fixed or secured in the second position. It is understood that other embodiments of the securing element 33 are of course also possible.

According to a particularly preferred embodiment, the tube pinch element 31 is arranged to be replaceable in the closing cover 3, so that the tube pinch element 31 can be replaced in a simple manner with another tube pinch element 31, for example one of a different size.

For this purpose, the closing cover 3 preferably comprises a recess 34 into which the tube pinch element 31 can be inserted. In FIG. 3, the tube pinch element 31 is represented outside the recess 34 for a better understanding. As indicated by the two arrows without reference signs in FIG. 3, the tube pinch element 31 can be easily inserted into or removed from the recess 34 in the closing cover 3. Preferably, the recess 34 comprises two lateral grooves that surround and guide the tube pinch element 31 so that the tube pinch element 31 is secured in the recess 34.

The tube pinch element 31 comprises two lateral tube supports 35, which are each designed in a flat, rounded U-shaped or V-shaped manner, so that the tube 100 is partially surrounded by the tube supports 35. Furthermore, the tube pinch element 31 comprises a central pinch element 36, which is arranged centrally between the two tube supports 35 and is designed in a rounded, preferably convexly rounded, manner on its side 31 facing the tube 100 in the operating state. In the operating state, the tube 100 is clamped off between the closing piece 21 and the central pinch element 36 of the tube pinch element 31 in the closed position of the closing element 2.

Preferably, several replaceable tube pinch elements 31 are provided so that for a specific application the suitable tube pinch element 31 can be selected according to the dimensions of the tube 100, in particular the outer diameter and/or the inner diameter of the tube 100. For example, for a tube 100 with a smaller outer diameter and/or smaller inner diameter, such a tube pinch element 31 can be used which has a higher central pinch element 36, i.e., which extends further into the receptacle 4, than a tube pinch element 31 which is provided for a tube 100 with a larger outer diameter and/or inner diameter.

The shape and design of the tube supports 35 can also be varied for different tube pinch elements 31.

Furthermore, it is preferred that a protective element 25 movable in the axial direction A is provided, which is loaded by a spring 27 in such a way that the protective element 25 covers the two lateral openings 32 when the closing cover 3 is in the first position represented in FIG. 3. The protective element 25 comprises two side walls 251 which are arranged on both sides of the closing piece 21, so that the closing piece 21 is located between the two side walls 251. The side walls 251 are arranged internally in the closure housing 13, each in front of one of the lateral openings 32. With respect to the axial direction A, the side walls 251 are dimensioned such that they preferably terminate flush with the lateral openings 32 in the first position of the closing cover 3 (FIG. 3), i.e., they completely cover the lateral openings 32 and do not protrude beyond the lateral openings 32 in the axial direction A. If no tube 100 is inserted in the pinch valve system 1, the two lateral openings 32 are thus completely covered by the side walls 251 of the protective element 25 both in the first position and in the second position, and thus serve as finger guards with which an unintentional reaching into the lateral openings 32 is prevented.

In other embodiments, the side walls 251 can also be designed to be somewhat shorter with respect to the axial direction so that they do not completely close the lateral openings, but preferably to such a degree that they prevent unintentional contact with a finger.

Furthermore, guide rails 26 are disposed in the closure housing 13, which guide the protective element 25 in the axial direction A, so that the protective element 25 can be moved back and forth in the axial direction A along the guide rails 26. The spring 27 is provided between the protective element 25 and the closing element 2, which is arranged such that it preloads the protective element 25 into the position represented in FIG. 3, in which the side walls 251 of the protective element 25 completely cover the lateral openings 32. Thus, for inserting a tube 100 into the receptacle 4, the protective element 25 must be moved against the force of the spring 27 in such a way that the side walls 251 at least partially uncover the lateral openings 32. If a tube 100 is inserted into the receptacle 4, the protective element 25 is moved in the axial direction with the tube 100 against the force of the spring 27 until the tube 100 lies in the receptacle 4 and in the lateral opening 32. Subsequently, the closing cover 3 is brought into the second position and secured there by the securing element 33.

The protective element 25 with the two side walls 251 further serves to center the tube 100, in particular in the case of tubes 100 that have a small outer diameter. The tube 100 is additionally fixed by the side walls 251, so that even for tubes 100 having a small outer diameter, it is reliably prevented that the tube 100 can move relative to the receptacle 4 when the closing cover 3 is in the second position (see FIG. 4). Furthermore, the protective element 25 prevents an uneven pinching of the tube 100 as well as eccentric introduction of force into the closing piece 21.

Figure 7:
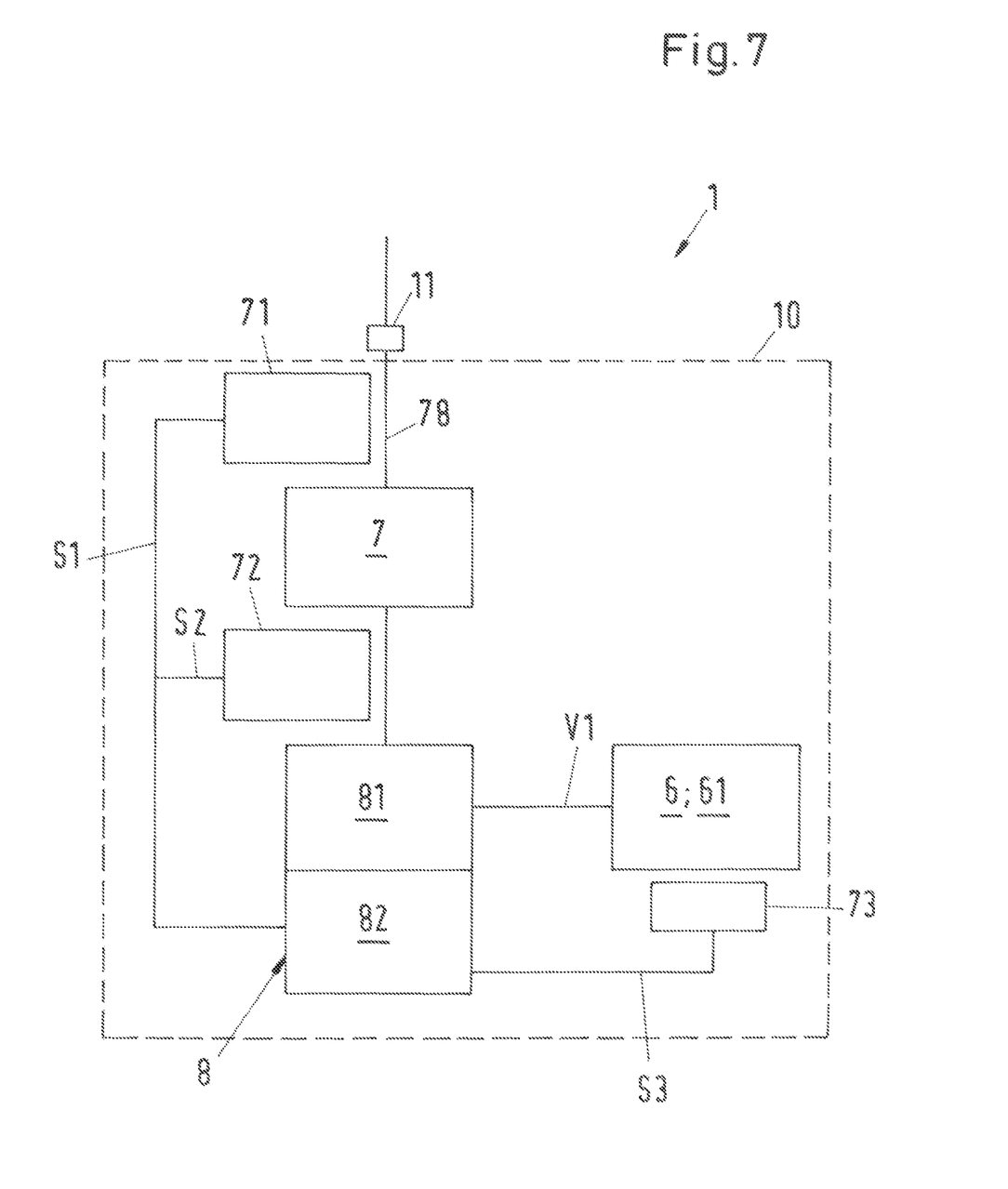
FIG. 7: illustrates as FIG. 5, but for a first variant of the embodiment.

In a representation corresponding to FIG. 5, FIG. 7 shows a first variant of the previously described embodiment. In this first variant, a measuring sensor 72 is additionally provided for determining the level or amount of energy stored in the energy storage device 7. The measuring sensor 72, which can be designed as a voltage sensor, for example, is signal-connected to the open loop control unit 82 of the control unit 8 via a signal line S2. The measuring sensor 72 monitors the energy storage device 7 and enables at least an estimation whether a switching process can still be carried out with the energy available in the energy storage device 7. For example, the measuring sensor 72 can be designed as a voltage measuring unit which is arranged in such a way that the electrical voltage at the capacitor can be measured. The electrical energy stored in the capacitor can then be at least estimated from the voltage at the capacitor of the energy storage device 7. The energy currently stored in the capacitor can then be compared, for example in the open loop control unit 82, with the electrical energy required for a switching process.

As a further option, it is possible to provide a position sensor 73 for determining the position of the closing element 2. For this purpose, any sensor known per se is suitable with which the position of the closing element 2 can be determined. In particular, it can be recognized by the position sensor 73 whether the closing element 2 is in the open position or in the closed position. The position sensor 73 is signal-connected to the open loop control unit 82 of the control unit 8 via a signal line S3.

When an interruption in the energy supply from the external power source is detected by the monitoring sensor 71, the open loop control unit 82 checks which is the predetermined rest position. The open loop control unit 82 receives information from the position sensor 73 about the current position of the closing element 2, namely whether the closing element 2 is in the open position or in the closed position. If the current position of the closing element 2 corresponds to the rest position, no further measures are required, and no further action is taken. If the current position of the closing element 2 does not correspond to the predetermined rest position, the open loop control unit 82 issues a command to the power unit 81 that a switching process is to be carried out. The actuating device 6 is controlled accordingly, and thus the closing element 2 is moved to the desired rest position. Then, it can be additionally checked by the position sensor 73 whether the closing element 2 has reached the predetermined rest position.

Of course, it is not necessary, but possible, that both a position sensor 73 and a measurement sensor 72 are provided. In other embodiments, only the position sensor 73 and no measurement sensor 72 can be provided. In still other embodiments, only the measurement sensor 72 and no position sensor 73 can be provided.

Figure 8:
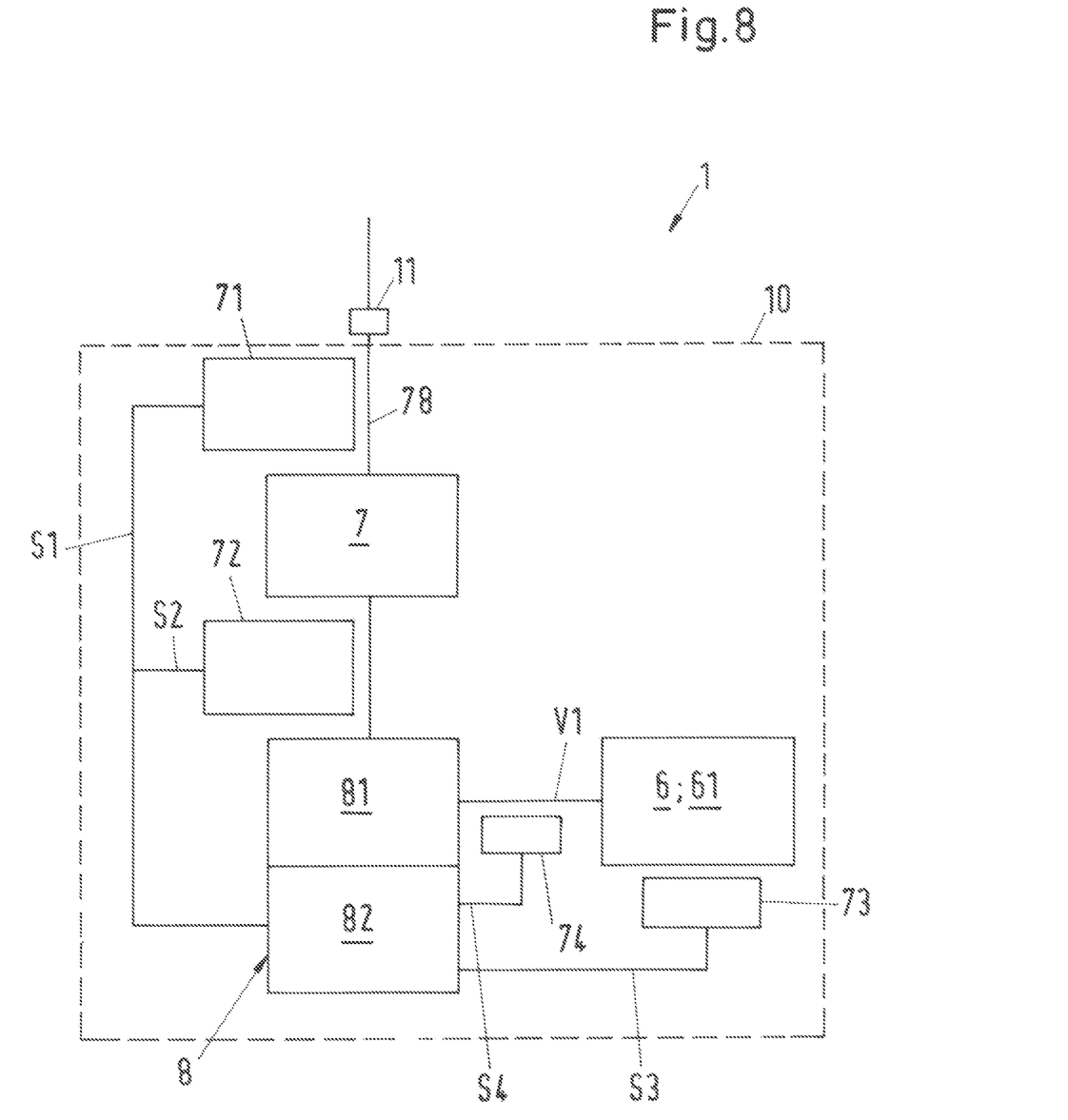
FIG. 8: illustrates as FIG. 5, but for a second variant of the embodiment.

In a representation corresponding to FIG. 5, FIG. 8 shows a second variant of the described embodiment. In this second variant, in comparison to the first variant (FIG. 7), a current sensor 74 is additionally provided for determining a switching current, which is signal-connected to the open loop control unit 82 of the control unit 8 via a signal line S4. The switching current is the electrical current required for the respective switching process.

The switching current can be a closing current, wherein the closing current is the electric current which is required for the switching process from the open position of the closing element 2 to the closed position of the closing element 2.

The switching current can be an opening current, wherein the opening current is the electrical current which is required for the switching process from the closed position of the closing element 2 to the open position of the closing element 2.

Therefore, the current sensor 74 is arranged and designed such that it can determine the current fed into the actuating device 6, in particular the current fed into the coil 61 of the actuating device 6. By the current sensor 74, the electric current which is required for the switching process from the open position to the closed position or from the closed position to the open position can be determined over the entire stroke of the closing element 2 from the open position to the closed position or from the closed position to the open position.

In particular, in this embodiment, it is possible that a tube detection on the basis of the switching current is carried out by the pinch valve system. For this purpose, correlations can be stored in an assignment table in the open loop control unit 82 of the control unit 8, for example, which closing current and/or which opening current is required for which type of tube in order to carry out a switching process from the open position to the closed position or vice versa. For example, the type of tube can contain information about the respective material of the tube, the outer diameter, the inner diameter, the wall thickness and, if necessary, other parameters. The assignment table is then, for example, a multi-dimensional table in which the correlations between the values that determine the type of tube and the required switching currents are stored. On the basis of the switching current captured by measurement and, if necessary, the signal from the position sensor 73, it is then possible to identify the tube 100 inserted into the pinch valve system 1.

Furthermore, it is possible to detect whether a tube 100 is inserted into the receptacle 4 of the pinch valve system 1 or not on the basis of a switching process carried out from the closed position to the open position or from the open position to the closed position and the measured detection of the switching current required for this.

Of course, such embodiments are also possible in which the tube detection is carried out only on the basis of the closing current or only on the basis of the opening current. A plurality of switching processes can also be carried out for the tube detection, and the required opening current or closing current can be measured in each case. For example, a switching process can be carried out from the open position to the closed position and then a switching process from the closed position to the open position.

In particular, the tube detection can also be carried out on a tube 100 that does not yet have fluid flowing through it, i.e., for example, on an empty tube 100.

What is claimed is:

1. A pinch valve system for clamping off a tube in a fluid system, comprising:

a closing element arranged movably in an axial direction and comprising a closing piece configured to clamp off the tube;

a permanent magnetic holding device comprising a permanent magnet configured to hold the closing element only by a permanent magnetic force in two different stable equilibrium positions, the two different stable equilibrium positions being an open position and a closed position, without energy being supplied to the permanent magnetic holding device for holding the closing element in the respective two different stable equilibrium positions;

an electromagnetic actuating device configured to carry out a switching process, with which the closing element is configured to be moved from the open position to the closed position or from the closed position to the open position;

an energy storage device configured to store an electrical energy which is at least sufficient to carry out the switching process; and a controller programmed with a predetermined rest position, which is the open position or the closed position, and the controller configured to trigger the switching process with which the closing element is brought to the rest position by the energy stored in the energy storage device.

2. The pinch valve system according to claim 1, wherein the closing element, the holding device, the actuating device, the energy storage device and the controller are arranged in a common housing, the housing having a connection configured to connect to an external energy source.

3. The pinch valve system according to claim 2, further comprising a monitoring sensor disposed in the common housing, the monitoring sensor configured to detect an interruption of the energy supply by the external energy source.

4. The pinch valve system according to claim 1, wherein the permanent magnetic holding device comprises a permanent magnetic ring surrounding the closing element.

5. The pinch valve system according to claim 1, wherein the energy storage device is an intermediate circuit for the energy supply of the actuating device.

6. The pinch valve system according to claim 1, further comprising a position sensor configured to determine a position of the closing element.

7. The pinch valve system according to claim 1, further comprising a measuring sensor configured to determine an amount of the electrical energy stored in the energy storage device.

8. The pinch valve system according to anyone of the preceding claims, further comprising a current sensor configured to determine a switching current, the switching current being the current required for the switching process.

9. The pinch valve system according to claim 8, wherein the pinch valve system enables a tube detection to be carried out on the basis of the switching current.

10. The pinch valve system according to claim 2, wherein the common housing includes two lateral openings to receive a tube, a closing cover is connected to the common housing by an articulated joint and is configured to be moved back and forth between a first position and a second position, in the first position the tube is capable of being inserted into the lateral openings, and in the second position the tube is fixed relative to the common housing of the pinch valve system.

11. The pinch valve system according to claim 10, wherein a tube pinch element is arranged in the closing cover to cooperate with the closing piece of the closing element such that the tube is capable of being clamped between the closing piece and the tube pinch element when the closing cover is in the second position.

12. The pinch valve system according to claim 11, wherein the tube pinch element is designed and arranged to be replaceable.

13. The pinch valve system according to claim 12, wherein the closing cover includes a recess into which the tube pinch element is capable of being inserted.

14. A pinch valve system for clamping off a tube in a fluid system, comprising:
   a closing element arranged movably in an axial direction and comprising a closing piece configured to clamp off the tube;
   a permanent magnetic holding device configured to hold the closing element by a permanent magnetic force in two different stable equilibrium positions, the two different stable equilibrium positions being an open position and a closed position, without energy being supplied to the permanent magnetic holding device for holding the closing element in the respective two different stable equilibrium positions;
   an electromagnetic actuating device configured to carry out a switching process, with which the closing element is configured to be moved from the open position to the closed position or from the closed position to the open position;
   an energy storage device configured to store an electrical energy which is at least sufficient to carry out the switching process;
   a controller programmed with a predetermined rest position, which is the open position or the closed position, and the controller configured to trigger the switching process with which the closing element is brought to the rest position by the energy stored in the energy storage device; and
   a protective element movable in the axial direction and configured to be loaded by a spring so that the protective element covers two lateral openings when the closing cover is in the first position or in the second position without the tube being inserted into the pinch valve system.

15. The pinch valve system according to claim 10, further comprising a securing element on the housing, the securing element configured to fix the closing cover in the second position.

16. A pinch valve system for clamping off a tube in a fluid system, comprising:
   a closing element arranged movably in an axial direction and comprising a closing piece configured to clamp off the tube:
   a permanent magnetic holding device configured to hold the closing element by a permanent magnetic force in two different stable equilibrium positions independently without use of a spring, the two different stable equilibrium positions being an open position and a closed position, without energy being supplied to the permanent magnetic holding device for holding the closing element in the respective two different stable equilibrium positions;
   an electromagnetic actuating device configured to carry out a switching process, with which the closing element is configured to be moved from the open position to the closed position or from the closed position to the open position;
   an energy storage device configured to store an electrical energy which is at least sufficient to carry out the switching process; and
   a controller programmed with a predetermined rest position, which is the open position or the closed position, and the controller configured to trigger the switching process with which the closing element is brought to the rest position by the energy stored in the energy storage device.

* * * * *